United States Patent [19]

Lafon

[11] 4,146,728
[45] Mar. 27, 1979

[54] ESTERS OF 2-[4-(4-CHLOROBENZOYL)-PHENOXY]-2-METHYL-PROPIONIC ACID WITH BIS-(HYDROXYALKYLTHIO)-ALKANES

[75] Inventor: Louis Lafon, Paris, France

[73] Assignee: Laboratoire L. Lafon, Maisons Alfort, France

[21] Appl. No.: 781,484

[22] Filed: Mar. 25, 1977

[30] Foreign Application Priority Data

Apr. 2, 1976 [GB] United Kingdom ............... 13486/76

[51] Int. Cl.$^2$ ............................................ C07C 69/76
[52] U.S. Cl. ...................................... 560/52; 424/308
[58] Field of Search ........................... 560/52; 424/308

Primary Examiner—Paul J. Killos
Attorney, Agent, or Firm—Poms, Smith, Lande, Glenny & Rose

[57] ABSTRACT

Esters of 2-[4-(4-chlorobenzoyl)-phenoxy]-2-methyl-propionic acid and bis-(hydroxyalkylthio)-alkanes of the formula:

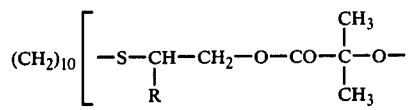
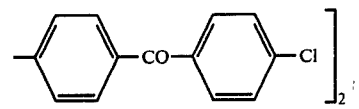

in which R is hydrogen or methyl are particularly useful in the prevention and treatment of hyperlipidaemia and hypercholesterolaemia.

6 Claims, No Drawings

ESTERS OF 2-[4-(4-CHLOROBENZOYL)-PHENOXY-2-METHYL-PROPIONIC ACID WITH BIS-(HYDROXYALKYLTHIO)-ALKANES

The present invention relates to certain esters of 2-[4-(4-chlorobenzoyl)-phenoxy]-2-methylpropionic acid with bis-(hydroxyalkylthio)-alkanes and to their therapeutic application, especially in the treatment of cardiovascular diseases.

It is known that the bis-(hydroxyalkylthio)-alkanes of the formula

HO—A—S—(CH$_2$)$_n$—S—A—OH (in which n is an integer from 5 to 15 and A represents a linear or branched C$_2$-C$_6$ hydrocarbyl group which can contain an OH group, particularly compounds in which A is —CH$_2$CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —C(CH$_3$)$_2$C(CH$_2$)$_2$—, —CH$_2$CHOHCH$_2$—, —CH(CH$_2$OH)CH$_2$CH$_2$—, —CH$_2$CH$_2$CH$_2$— or —CH$_2$CH(CH$_3$)CH$_2$— are useful as hypo-lipidaemic and hypo-cholesterolaemic agents (see for example, British Patent Specification No. 1,307,227, French Pat. No. 2,146,138 and British Patent Application No. 41381/74).

It is also known that 2-[4-(4-chlorobenzoyl)-phenoxy]-2-methylpropionic acid and its esters, in particular isopropyl 2-[4-(4-chlorobenzoyl)-phenoxy]-2-methylpropionate (which has been marketed under the name LIPANTYL) are useful as hypolipidaemic and hypocholesterolaemic agents (see French Pat. No. 2,157,853).

The present invention is based on the surprising discovery that the esters obtained from 2-[4-(4-chlorobenzoyl)-phenoxy]-2-methylpropionic acid and 3,14-dithia-1,16-hexadecanediol or 2,15-dimethyl-3,14-dithia-1,16-hexadecanediol have valuable properties which differ from the combined properties of the acid and either of the diols.

Accordingly, the present invention provides esters of 2-[4-(4-chlorobenzoyl)-phenoxy]-2-methylpropionic acid and bis-(hydroxyalkylthio)-alkanes of the formula

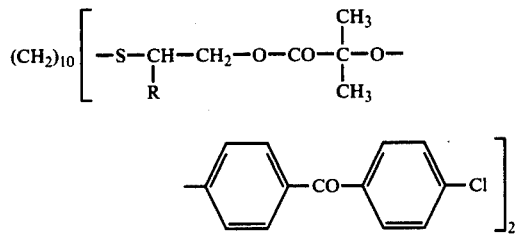

in which R is hydrogen or methyl.

These esters, which are novel per se, can be prepared by methods known per se. The preferred process consists of reacting 1 mol of 3,14-dithia-1,16-hexadecanediol or of 2,15-dimethyl-3,14-dithia-1,16-hexadecanediol with at least 2 mols of 2-[4-(4-chlorobenzoyl)-phenoxy]-2-methylpropionyl chloride in the presence of a base (preferably an amine).

The invention also provides a therapeutic composition containing at least one ester of 2-[4-(4-chlorobenzoyl)-phenoxy]-2-methylpropionic acid with 3,14-dithia-1,16-hexadecanediol or 2,15-dimethyl-3,14-dithia-1,16-hexadecanediol, in association with a physiologically acceptable excipient.

The invention is illustrated by the following Examples:

EXAMPLE 1

1,16-(3,14-Dithia-hexadecyl) di-[2-[4-(4-chlorobenzoyl)-phenoxy]-2-methylpropionate]

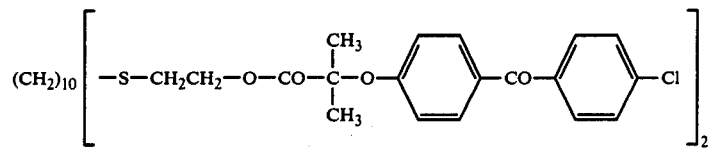

Code No. : CRL 40,376

(a) 2-[4-(4-Chlorobenzoyl)-phenoxy]-2-methylpropionyl chloride 18.6 ml (0.25 mol) of thionyl chloride are added to a solution of 31.85 g (0.10 mol) of 2-[4-(4-chlorobenzoyl)-phenoxy]-2-methylpropionic acid in 100 ml of anhydrous benzene and the mixture is then heated under reflux for 1 hour 30 minutes. After cooling, the solvent and the excess chlorinating agent are driven off under reduced pressure. The residual chestnut-coloured crystalline mass is taken up in petroleum ether. After filtering, washing and drying, 28 g of the expected acid chloride are obtained, in the form of a beige powder. Instanteous melting point (Köfler) = 80°–81° C. Yield = 83.2%.

(b) CRL 40,376

1.8 ml (22 mmols) of pyridine are added to a solution of 1 g (3.4 mmols) of 3,14-dithia-1,16-hexadecanediol (Code No. LL 1,558) and 5 g (14.8 mmols) of the above acid chloride in 25 ml of anhydrous benzene. The mixture is heated under reflux for 16 hours, cooled, taken up in ether and acidified with a solution of hydrochloric acid. After decanting, the ether is washed with a 4% strength sodium carbonate solution and then with water, and dried. After evaporation, a crystalline paste is obtained, which is taken up in ether and is left in an ice-box for 24 hours. A yellow crystalline product is then filtered off. The filtrate, evaporated to dryness, leaves a limpid orange-brown oil (2.3 g) which is pure according to thin layer chromatography. Yield = 76%.

EXAMPLE 2

(±) 1,16-(2,15-Dimethyl-3,14-dithia-hexadecyl) di-[2-[4-(4-chlorobenzoyl)-phenoxy]-2-methylpropionate]

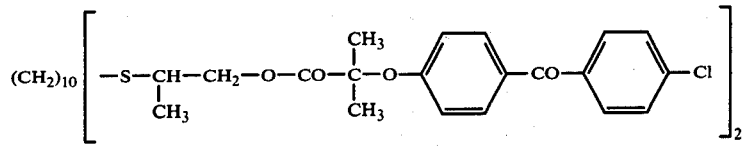

Code No. : CRL 40,397

1.6 ml of pyridine are added to 2.1 g (6.5 mmols) of (±)-2,15-dimethyl-3,14-dithia-1,16-hexadecanediol (Code No. CRL 40,122) in 15 ml of dry benzene, and a solution of 6 g (17.8 mmols) of the acid chloride prepared in Example 1 (a), in 15 ml of benzene, is then added to this solution over the course of 20 minutes. The mixture is heated for 7 hours with the benzene refluxing and is then cooled and taken up in ether. The ether is washed with water, dried and then evaporated. 7.9 g of an oil are obtained, in which a crystalline product appears. The whole is taken up in 50 ml of a 50:50 v/v mixture of cyclohexane and petroleum ether and filtered. The filtrate is evaporated and the oily residue is dissolved in benzene. The benzene liquor is filtered and then chromatographed on 50 g of silica. The expected ester is diluted with chloroform. 1.6 g of a limpid pale yellow oil are obtained, which has a slight odour and is pure according to thin layer chromatography. Yield = 26.7%.

The results of experiments which were carried out on animals in order to examine the physiological effects of the esters of the invention are summarised below. The test procedure was as follows: rats given a normal diet received the products to be tested in daily doses of 10 mg/kg, 20 mg/kg, 50 mg/kg and 100 mg/kg orally for 3 and 5 days (two durations for each dose).

A reduction in the concentration of the cholesterol and of the lipids of the blood plasma was observed. In particular it was noted that in rats, CRL 40,397 (the product of Example 2) brought about a reduction in the blood cholesterol of 30% (relative to comparison rats) and a reduction of the blood lipids of 24% (relative to comparison rats) after oral administration of 100 mg/kg for 4 days.

Clinical trials yielded information relating to the treatment and prevention of hyperlipidaemia and hypercholesterolaemia, and as a result led to the recommendation of the following dosages:

oral administration of CRL 40,376 and CRL 40,397, more particularly as gelules or capsules, such that one gelule or capsule, containing from 200 mg to 600 mg of active ingredient, is taken from 2 to 4 times per day for at least one week.

I claim:

1. Esters of 2-[4-(4-chlorobenzoyl)-phenoxy]-2-methylpropionic acid and bis-(hydroxyalkylthio)-alkanes of the formula:

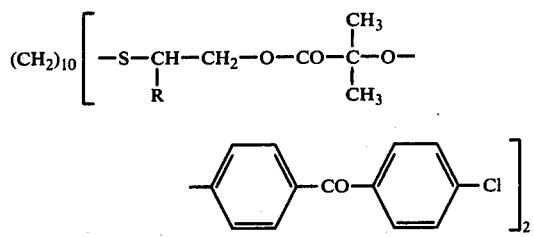

in which R is hydrogen or methyl.

2. 1,16-(3,14-Dithia-hexadecyl)di-[2-[4-(4-chlorobenzoyl)-phenoxy]-2-methylpropionate].

3. (±) 1,16-(2,15-Dimethyl-3,14-dithia-hexadecyl)-di[2-[4-(4-chlorobenzoyl)-phenoxy]-2-methylpropionate].

4. A therapeutic composition comprising as active ingredient at least one ester as claimed in claim 1, in association with a physiologically acceptable excipient.

5. A method of treating or preventing hyperlipidaemia and hychlolesterolaemia which comprises administering to the patient a compound as claimed in claim 1.

6. A method according to claim 5, in which gelules or capsules, each containing from 200 mg to 600 mg of active ingredient are orally administered to the patient.

* * * * *